(12) United States Patent
Yasuda et al.

(10) Patent No.: US 6,614,042 B2
(45) Date of Patent: Sep. 2, 2003

(54) WORKPIECE INSPECTING DEVICE

(75) Inventors: Nobuyuki Yasuda, Osaka (JP); Masatoshi Yasuda, Osaka (JP)

(73) Assignee: Kabushiki Kaisha Yutaka, Osaka (JP)

( * ) Notice: Subject to any disclaimer, the term of this patent is extended or adjusted under 35 U.S.C. 154(b) by 50 days.

(21) Appl. No.: 09/976,015

(22) Filed: Oct. 15, 2001

(65) Prior Publication Data

US 2002/0043635 A1 Apr. 18, 2002

(30) Foreign Application Priority Data

Oct. 17, 2000 (JP) ........................ 2000-316531

(51) Int. Cl.[7] ............... G01N 21/88; G01N 21/00; G06M 7/00
(52) U.S. Cl. .................. 250/559.45; 250/222.1; 250/221; 356/237.6
(58) Field of Search ............. 250/559.45, 223 R, 250/221, 222.1, 559.1; 356/237.1, 237.6

(56) References Cited

U.S. PATENT DOCUMENTS 4,975,568 A * 12/1990 Taniguchi et al.

* cited by examiner

*Primary Examiner*—David Porta
*Assistant Examiner*—David C Meyer
(74) *Attorney, Agent, or Firm*—Wenderoth, Lind & Ponack, L.L.P.

(57) ABSTRACT

A workpiece inspecting device suitable for inspection of tiny workpieces is provided which move workpieces such as screws, nails, screws and rivets while hanging them in the air and to carry out overall length inspection and projecting inspection of the workpieces while they are moving. A hanging portion is provided on the outer periphery of the turntable to lower the position of the bottom surface of the turntable at the outer peripheral portion where the workpieces are supported, so that the heads of workpieces supported in a hanged state from the turntable are within an inspection area through windows provided in the hanging portion.

9 Claims, 8 Drawing Sheets

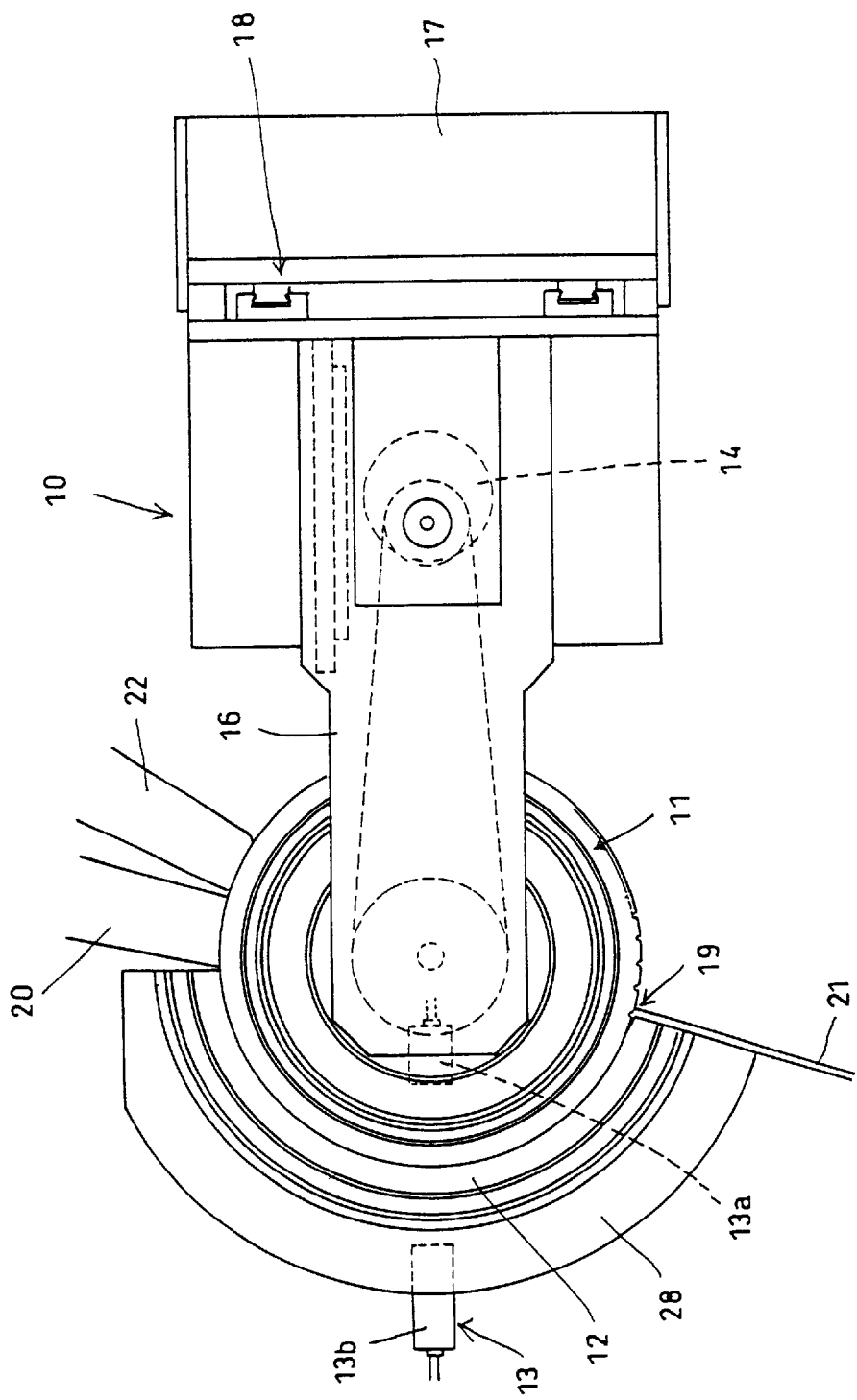

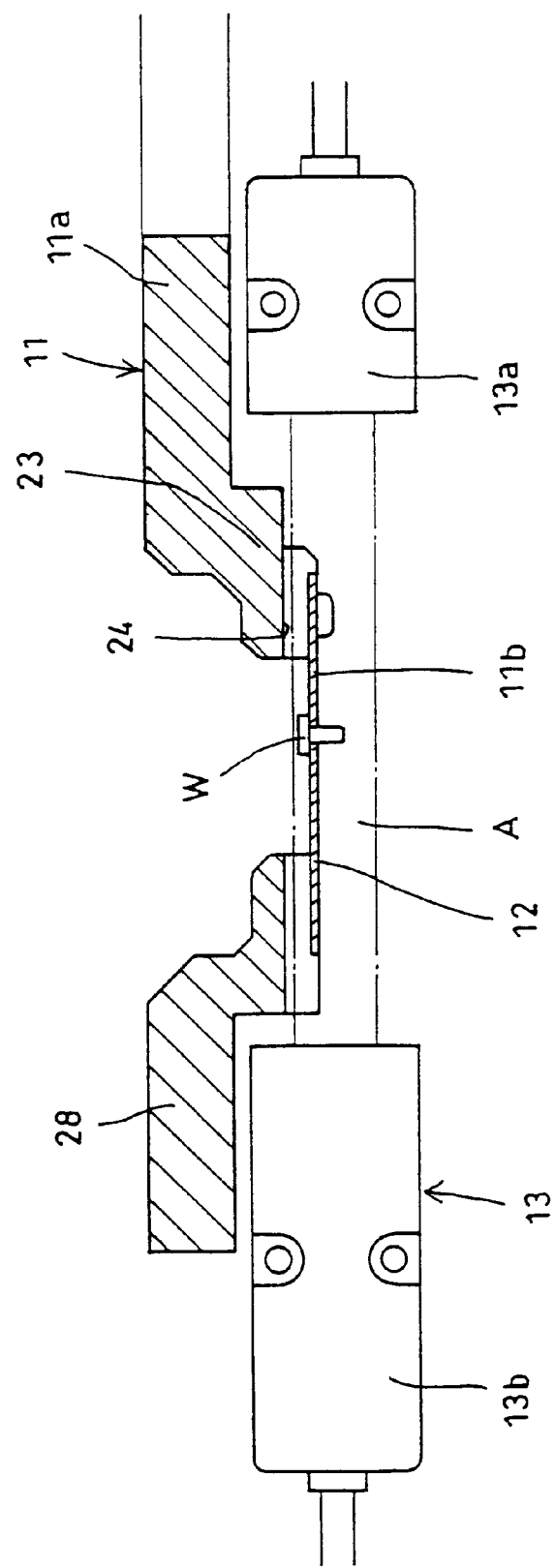

WORKPIECE INSPECTING DEVICE

BACKGROUND OF THE INVENTION

This invention relates to a workpiece inspecting device for inspecting parts (workpieces) with heads, such as screws, nails and rivets, while moving them using a turntable.

There is known a device in which neck portions of workpieces supplied from a feeder are received in notches formed in the outer periphery of a turntable at regular pitches and the workpieces are moved by rotation of the turntable while supporting the heads of the workpieces on the top surface of the table to check the lengths of the workpieces below their neck portions. Such devices have an advantage that a workpiece introducing portion, an inspecting portion, a portion for ejecting defective workpieces and a portion for taking out non-defectives can be arranged along a circular orbit, so that it can be made small.

A conventional inspecting device of this type is shown in FIG. 8. It has a turntable 1 and a guide 2 provided along the outer periphery of the turntable 1. On the outer periphery of the turntable, notches 3 for receiving necks of workpieces are provided at regular pitches. It supports the heads of the workpieces W on the top surface of the outer periphery of the table 1 and moves the workpieces hanging in the air while preventing them from coming out of the notches 3 with the guide 2. At an intermediate portion of the moving path, a light-emitting portion 4 and a light-receiving portion 5 of an optical sensor are provided opposite to each other. When passing there, the length under the neck of each workpiece is inspected. Any workpiece that has been judged defective in this inspection is ejected at an ejecting portion, so that only non-defectives flow to the takeout portion.

With this conventional inspecting device, since inspection is carried out under the table 1, it is impossible to carry out inspection of overall length of the workpieces or projecting inspection from sideways.

Also, for inspection of the length under the neck, the length from the bottom surface of the table to the tip of each workpiece is measured (assuming that the distance from the bottom surface of the table to the optical path A is constant, partial length on the side of the tip of the workpiece may be measured as shown). But with this method, run-out (that is, vertical displacement) of the workpiece supporting surface (top surface of the table at its outer periphery) causes measurement error. This lowers the measuring accuracy.

Further, among the objects to be inspected, tiny workpieces are increasing (in particular, many screws are tiny). With a conventional inspecting device which has a thick table, no proper inspection is possible because the portion under the neck does not protrude from the bottom surface of the table or the protruding length is too short. As measures against this, if the thickness of the table is reduced, the table tends to be strained, so that the run-out of the workpiece supporting surface grows. In this case, too, proper inspection is impossible.

An object of this invention is to make it possible to carry out overall length inspection and projecting inspection of the entire part of workpieces, using a turntable.

SUMMARY OF THE INVENTION

According to the present invention, a turntable includes a hanging portion at outer periphery thereof so that the bottom surface of the turntable at the outer peripheral portion is lower than the bottom surface of the turntable at its center. The hanging portion is provided with windows so as to be opposite to notches. A light emitting portion and a light receiving portion of an optical sensor or a light source for illumination and a camera are arranged opposite to each other inside of the hanging portion and outside of the outer periphery of the turntable, respectively, so that the heads of the workpieces are in the inspecting area through the windows.

According to the present invention, the outer peripheral portion of the turntable is formed by an annular thin plate and the thin plate is fixed to the bottom of the hanging portion by a clamping tool. Thus even tiny workpieces can be inspected without trouble.

Preferably, the turntable is mounted to the bottom of a spindle arranged to extend downwardly and an elevator mechanism is provided to move the turntable in a vertical direction, and a driving means for rotating the spindle is provided.

This invention is also applicable to an inspecting device in which workpieces are transported by being placed on the top surface of the outer periphery of the turntable.

In this invention, because a hanging portion is provided at the outer peripheral portion of the turntable and the head of a workpiece can be taken into the inspecting area through the windows formed in the hanging portion, it is possible to carry out overall length inspection and projecting inspection of an entire workpiece.

Heretofore, overall length of the workpieces was inspected with the workpieces handing in the air by a wire. With this arrangement, displacement of workpieces occurs due to shaking of the wire. Thus, if the measuring timing is judged based on the position of workpieces, malfunction tends to occur. With the device according to this invention, since workpieces are supported by the turntable, which is less liable to shake, such malfunction will not occur.

Also, in the overall length inspection, it is possible to ignore run-out of the workpiece supporting surface. Thus it is possible to accurately determine the length below the neck by subtracting the height of the head from the actually measured overall length.

Further, in a conventional device for inspecting the length of the workpieces below the neck, for tiny workpieces of which the portion below the neck does not sufficiently protrude from the bottom surface of the table, it is impossible to carry out confirmation as to whether the workpieces are on the table. But the device of this invention can perform such confirmation based on the existence or nonexistence of the heads.

By forming the outer peripheral portion of the table from a thin plate, it is possible to inspect tiny workpieces without trouble.

If the outer peripheral portion of the table is thinned and is made integral, it is difficult to remove strain. According to this invention, a separate thin plate is fixed by a clamping tool to prevent strain. This suppresses shaking of workpieces while moving, making stable inspection possible.

By providing an elevator mechanism, it is possible to create a working space under the table by raising the turntable. The table is easily exchangeable.

Other features and objects of the present invention will become apparent from the following description made with reference to the accompanying drawings, in which:

BRIEF DESCRIPTION OF THE DRAWINGS

FIG. 2 is a plan view of the same;

FIG. 5 is an enlarged sectional view showing how a light-emitting and a light-receiving portion of an optical sensor are arranged;

DETAILED DESCRIPTION OF THE PREFERRED EMBODIMENT

Figure 1:
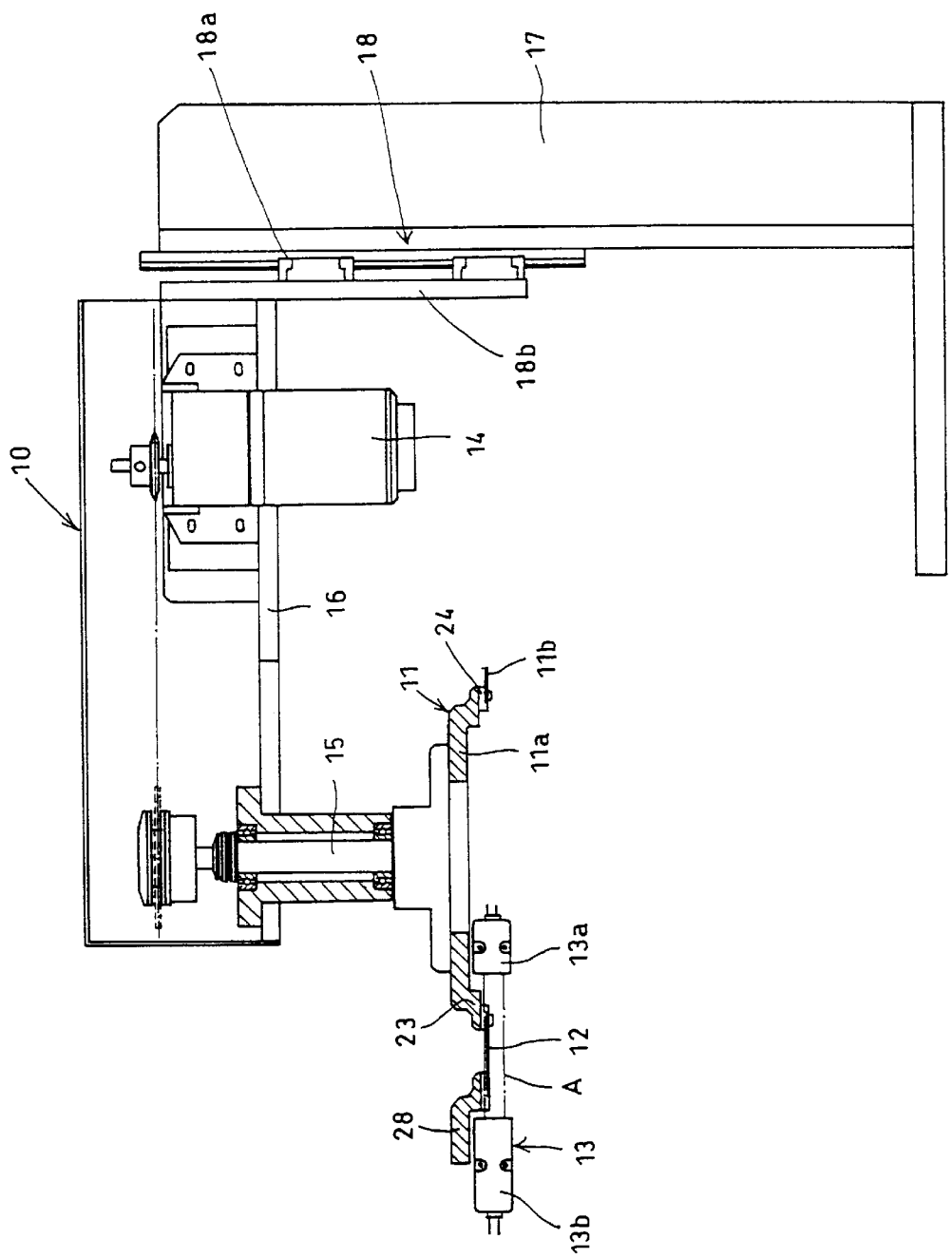
FIG. 1 is a sectional side view showing an embodiment of the inspecting device of this invention.

FIGS. 1 and 2 show an embodiment of the inspecting device according to this invention.

This inspecting device 10 has a turntable (table for short) 11, a guide 12 provided along the outer periphery of the table, and an optical sensor 13 provided in an inspecting portion.

The turntable 11 is mounted to the bottom end of a spindle 15 arranged to extend downwardly and rotated by a motor 14. The motor and the spindle 15 are mounted on a support arm 16, which is supported by a support pillar 17 and mounted to a slider 18b of an elevator mechanism 18 including a linear guide 18a. With this arrangement, it is possible to raise the turntable 11 to the terminal end of the stroke of the elevator mechanism 18 together with the support arm 16.

The guide 12 is, as shown in FIG. 2, provided within a range from a part introducing portion 19 to a part ejecting portion 20. Parts or workpieces fed by a feeder 21 are transferred onto the table 11 and toward a discharge portion 22 as the table rotates.

Figure 3A:
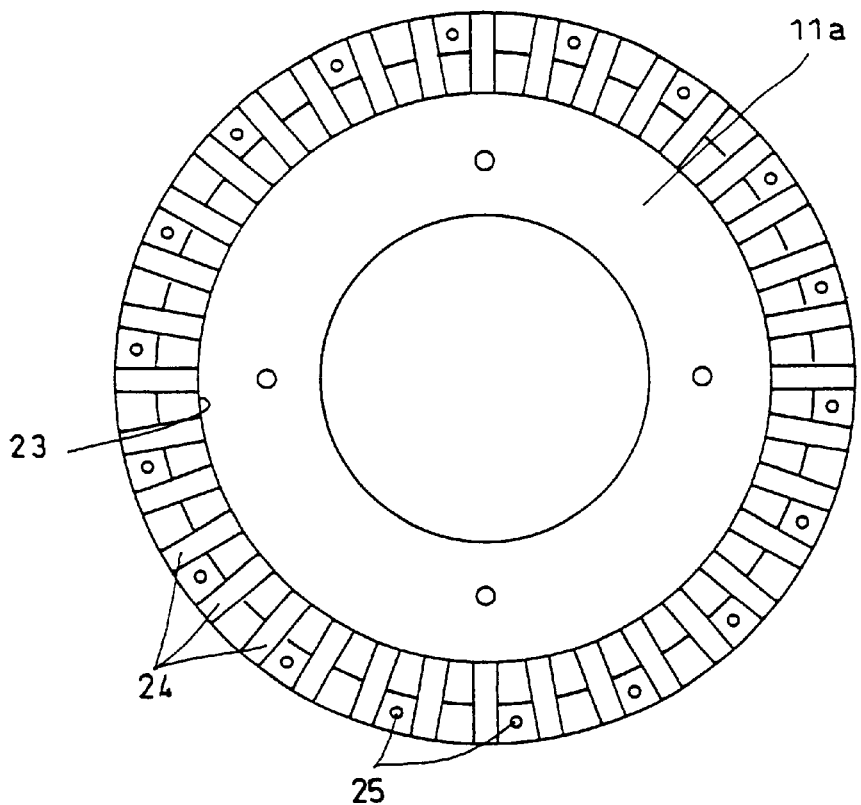
FIG. 3A is a bottom view showing an example of the body of the turntable.
Figure 3B:
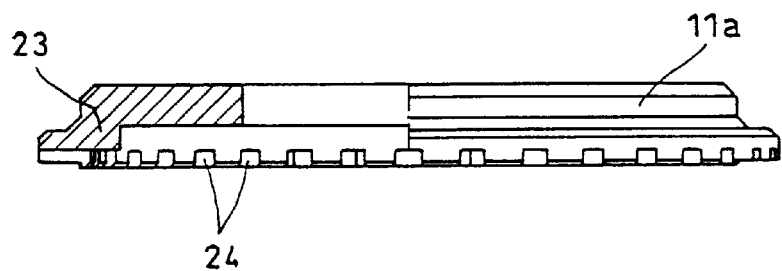
FIG. 3B is a partially cutaway side view of the same.
Figure 4A:
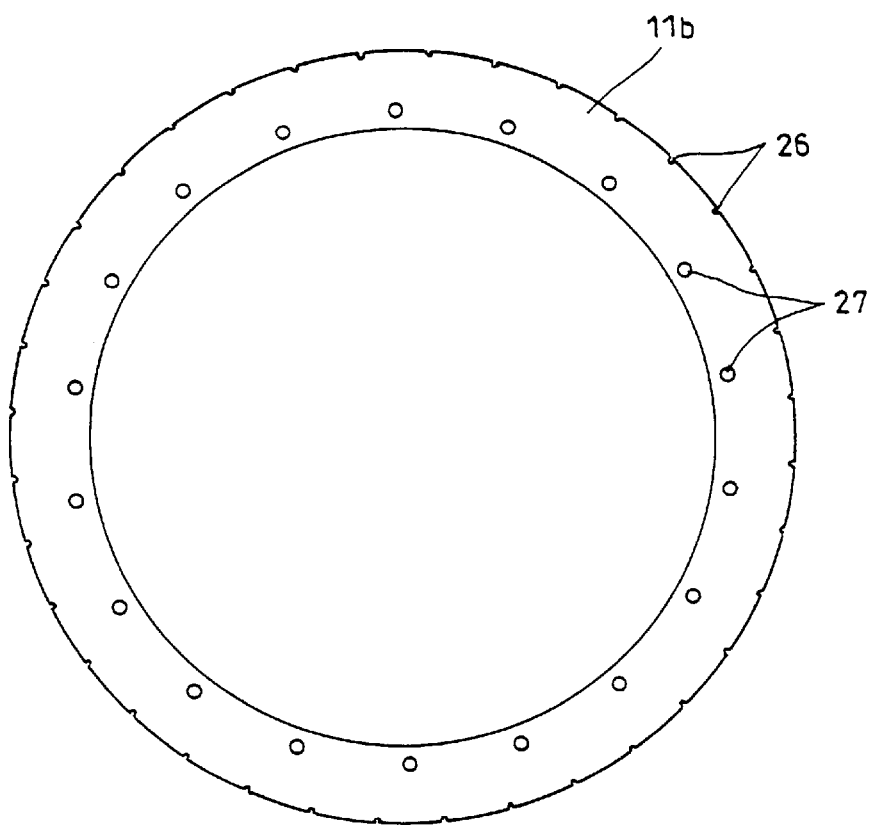
FIG. 4A is a plan view of an annular thin plate forming the outer peripheral portion of the turntable.
Figure 4B:
FIG. 4B is a sectional view of the thin plate.

FIGS. 3 and 4 show the structure of the turntable 11. The turntable of FIG. 1 is formed by combining a body portion 11a of FIG. 3 and an annular thin plate 11b of FIG. 4.

As shown in FIG. 3, the body portion 11a is formed with a hanging portion 23 on the outer periphery of an apertured disk and with radial slits 24 (which serve as windows) and threaded holes 25 in the bottom surface of the hanging portion 23 at regular pitch. By providing a hanging portion at outer periphery of the turntable, a recess is formed in the bottom surface of the turntable 11. As shown in FIG. 4, the thin plate 11b is formed in the outer periphery thereof with notches 26 at the same pitch as the slits 24 and mounting holes 27 corresponding to the threaded holes 25.

The turntable 11 is assembled by screwing the annular thin plate 11b to the bottom of the outer periphery of the body portion 11a. The thickness of the thin plate 11b is about 0.5–1.0 mm. In order to suppress strain of such a thin plate, a separate thin plate is secured by means of screws.

FIG. 5 is an enlarged view of a portion where an optical sensor 13 is installed. The optical sensor has a laser beam emitting portion 13a and a beam receiving portion 13b.

The beam emitting portion 13a and the beam receiving portion 13b are arranged opposite to each other inside of the hanging portion 23 and outside of the table, respectively.

Laser beams are passed through the windows formed by the slits 24 so that the entire portion of a workpiece W including the head, will be in the optical path A, i.e. in the inspecting region. Thus it is possible to conduct inspection for the overall length of the workpiece W and the length from its neck.

The guide 12 has the same thickness as and is arranged at the same height or level as the thin plate 11b so as not to interrupt the optical path (FIG. 5). The guide 12 is supported by a holder 28 at a position out of the optical path A.

Figure 6:
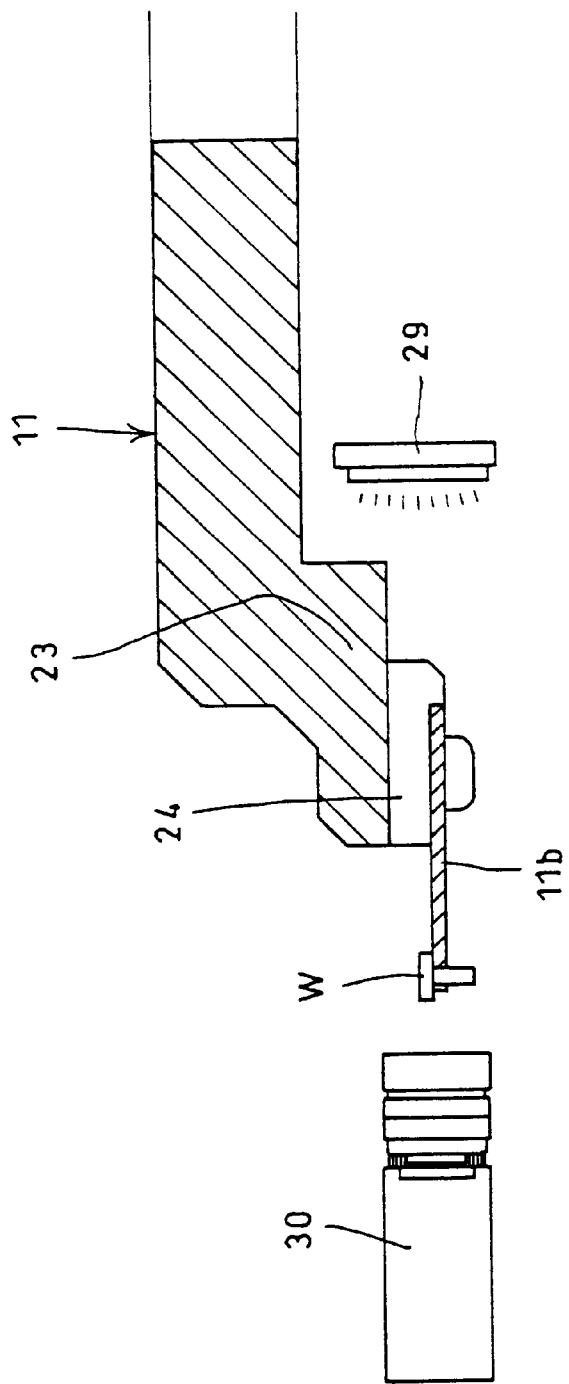
FIG. 6 is an enlarged sectional view of a projection inspecting portion using a light source and a CCD camera.

In FIG. 6, instead of the light emitting and receiving portions 13a, 13b in FIG. 6, a light source 29 for illumination and a CCD camera 30 are arranged opposite to each other. Projection inspection of external shapes, etc. can be done.

Figure 7:
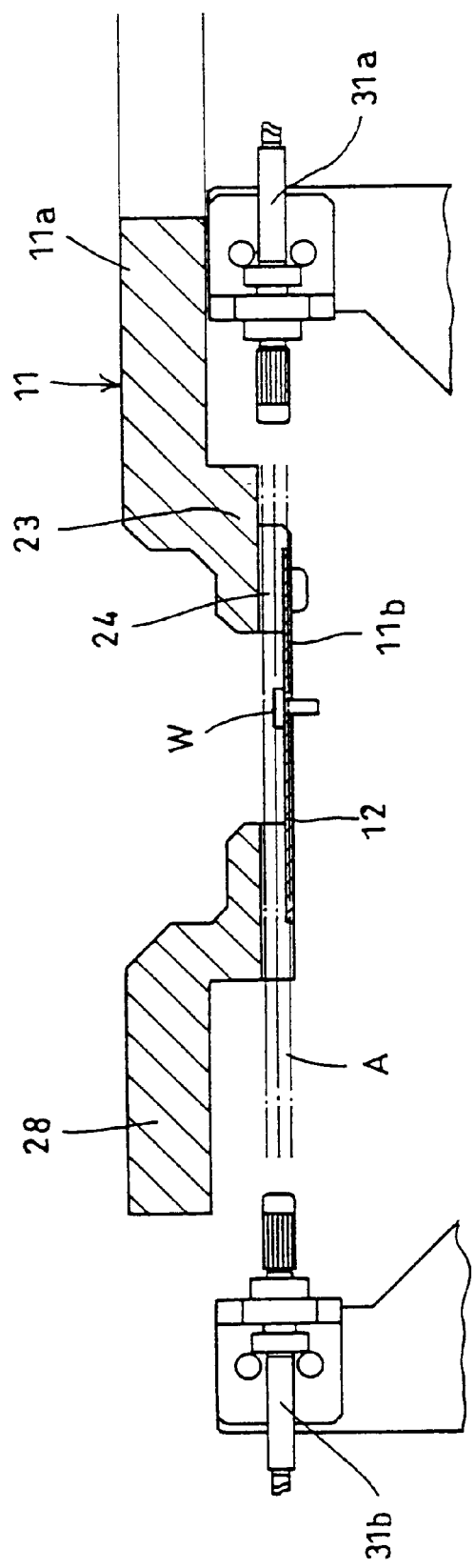
FIG. 7 is a view showing an example in which the light-emitting portion and light-receiving portion are formed by optical fibers.
Figure 8:
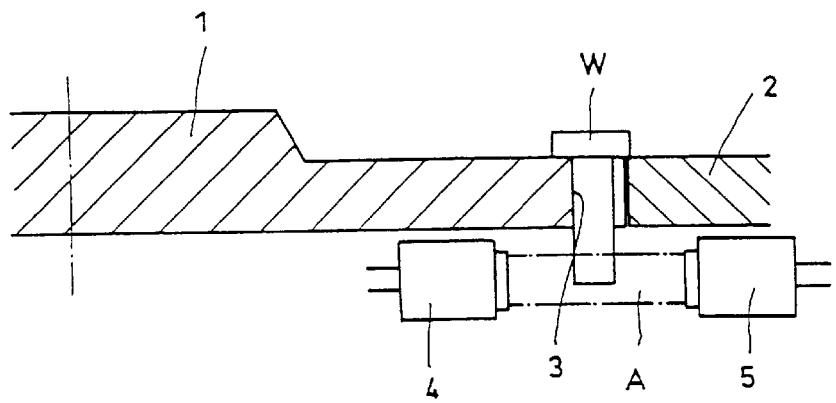
FIG. 8 is a sectional view schematically showing a conventional inspecting device.

In FIG. 7, optical fibers 31a and 31b connected to a light emitting element and a light receiving element (both not shown) of an optical sensor, respectively, are arranged opposite to each other, and the light projected from one of the optical fibers is passed through the windows formed by the slits 24 and entered into the other optical fiber. If the optical path is interrupted by the head of a workpiece W, the amount of light received decreases. Thus, even for a tiny workpiece, it is possible to confirm whether or not the workpiece is on the table 11.

It is preferable to make thin the outer peripheral portion of the table 11, because reliable inspection of tiny workpieces is possible. But the device of this invention can be used for inspection of workpieces of different sizes. There is no need to thin the outer peripheral portion of the table.

Also, the elevator mechanism 18 of FIG. 1 is provided for the purpose of simplifying exchange of the turntable 11. But this is not an essential element, either. A device in which the spindle 15 is arranged below the table 11 so as to face upward is conceivable. With such a device, since the table 11 can be dismounted from above, exchange is not difficult.

Further, it is also conceivable to provide an inspecting portion for overall length inspection, a projecting inspection portion and a portion for confirming the existence of workpieces on a single device.

Also, the above description has been made about a device in which workpieces are transported hanging. But this invention is also applicable to a device in which the notches 26 in the outer peripheral portion of the table 11 are omitted and inspection is done while transporting workpieces placed on the top surface of the table at its outer periphery. In such an arrangement, too, it is possible to carry out inspection making use of the advantages of the turntable.

As described above, according to this invention, since the position of the outer peripheral portion of the table is lowered by providing the hanging portion on the turntable so that the head of a workpiece can be taken into an inspection area through the windows formed in the hanging portion, it is possible to conduct overall length inspection of a workpiece or projecting inspection of its entire part. In the arrangement in which the outer peripheral portion of the table is formed by a thin plate, it is possible to carry out inspection of tiny workpieces, so that it can cope with a variety of workpieces.

In overall length inspection, since there is no influence of run-out of the workpiece supporting surface, the accuracy of inspection of the length below the neck improves.

Besides, it is possible to carry out confirmation inspection of a workpiece by the existence or non-existence of the head. Thus, a high-performance inspecting device is provided.

What is claimed is:

1. A workpiece inspecting device comprising a turntable for supporting workpieces on the top surface of its outer periphery, and an inspecting portion comprising an optical sensor or a camera for inspecting the workpieces, said turntable including a hanging portion at outer periphery thereof so that the bottom surface of said turntable at the outer peripheral portion is lower than the bottom surface of said turntable at its center, said hanging portion being provided with windows so as to be opposite to said notches, the light emitting portion and the light receiving portion of said optical sensor or the light source for illumination and the camera being arranged opposite to each other inside of said hanging portion and outside of the outer periphery of said turntable, respectively, so that the heads of the workpieces are in said inspecting area through said windows.

2. A workpiece inspecting device for inspecting a workpiece having a head portion, a neck portion and a lower portion, said inspecting device comprising:

a turntable having a radially inner portion, a radially outer portion, and a hanging portion between said radially inner portion and said radially outer portion, said turntable being operable to move a workpiece with its head portion protruding from a top surface of said radially outer portion of said turntable; and an inspection portion comprising an optical sensor operable to inspect the workpiece and having a light emitting portion operable to emit light and a light receiving portion operable to receive light, wherein said radially outer portion has a plurality of notches at regular pitches, each notch being operable to receive the neck portion of the workpiece, wherein said hanging portion has a shape such that the top surface of said radially outer portion is lower than the bottom surface of said radially inner portion, wherein said hanging portion is provided with windows so as to be opposite to said notches, and wherein one of the light emitting portion and the light receiving portion is provided under said radially inner portion and the other of the light emitting portion and the light receiving portion is provided radially outside of said turntable so that light from the light emitting portion passes through one of said windows to illuminate portions of the workpiece protruding from the top surface of said radially outer portion and passes through space under said radially outer portion to illuminate portions of the workpiece protruding downwardly from the bottom surface of said radially outer portion and is received by said light receiving portion.

3. A workpiece inspecting device as claimed in claim 2, wherein said radially outer portion of said turntable comprises an annular thin plate, and wherein said thin plate is fixed to the bottom of said hanging portion.

4. A workpiece inspecting device as claimed in claim 3, further comprising:

a spindle having an end attached to said turntable such that a longitudinal axis of said spindle is substantially parallel to an axis of rotation of said turntable;

an elevator mechanism operable to move said turntable in a direction substantially parallel to the axis of rotation of said turntable; and a driver operable to rotate said spindle.

5. A workpiece inspecting device as claimed in claim 3, further comprising:

a guide operable to prevent the workpiece from coming out of said turntable, said guide being provided along said radially outer portion of said turntable so as to extend from a workpiece introducing portion to a workpiece dispensing portion, wherein said guide has the same thickness as and is arranged at the same level as said radially outer portion of said turntable, and wherein said guide is supported at a position out of an inspecting area.

6. A workpiece inspecting device as claimed in claim 2, further comprising:

a spindle having an end attached to said turntable such that a longitudinal axis of said spindle is substantially parallel to an axis of rotation of said turntable;

an elevator mechanism operable to move said turntable in a direction substantially parallel to the axis of rotation of said turntable; and a driver operable to rotate said spindle.

7. A workpiece inspecting device as claimed in claim 6, further comprising:

a guide operable to prevent the workpiece from coming out of said turntable, said guide being provided along said radially outer portion of said turntable so as to extend from a workpiece introducing portion to a workpiece dispensing portion, wherein said guide has the same thickness as and is arranged at the same level as said radially outer portion of said turntable, and wherein said guide is supported at a position out of an inspecting area.

8. A workpiece inspecting device as claimed in claim 2, further comprising:

a guide operable to prevent the workpiece from coming out of said turntable, said guide being provided along said radially outer portion of said turntable so as to extend from a workpiece introducing portion to a workpiece dispensing portion, wherein said guide has the same thickness as and is arranged at the same level as said radially outer portion of said turntable, and wherein said guide is supported at a position out of an inspecting area.

9. A workpiece inspecting device as claimed in claim 2, wherein said light emitting portion comprises a light source operable to illuminate the workpiece, and wherein said light receiving portion comprises a camera operable to inspect the workpiece by receiving illumination from said light source.

* * * * *